United States Patent [19]

Walon

[11] 4,199,372
[45] Apr. 22, 1980

[54] PROCESS FOR PREPARING MALTOSE-CONTAINING STARCH HYDROLYZATE AND CRYSTALLIZATION OF MALTOSE THEREFROM

[75] Inventor: Raoul G. P. Walon, Brussels, Belgium

[73] Assignee: CPC International Inc., Englewood Cliffs, N.J.

[21] Appl. No.: 1,661

[22] Filed: Jan. 8, 1979

[30] Foreign Application Priority Data

Jan. 12, 1978 [GB] United Kingdom .................... 129/78

[51] Int. Cl.$^2$ ............................................. C12P 19/20
[52] U.S. Cl. ...................................... 127/40; 435/96; 435/99
[58] Field of Search ...................... 435/96, 99; 127/38, 127/40

[56] References Cited

U.S. PATENT DOCUMENTS

| 4,028,186 | 6/1977 | Sakai | ....................................... 435/99 |
| 4,032,403 | 6/1977 | Sakai et al. | ......................... 435/99 X |

*Primary Examiner*—Lionel M. Shaprio

[57] ABSTRACT

Crystalline maltose in good yields is obtained by subjecting a starch hydrolyzate having a maltose content of at least 75% and a viscosity of greater than 400 cps. to the action of glucoamylase, whereby the viscosity is reduced to below 400 cps. without any substantial reduction in the maltose content, and then subjecting the resulting hydrolyzate to a conventional crystallization operation.

6 Claims, No Drawings

PROCESS FOR PREPARING MALTOSE-CONTAINING STARCH HYDROLYZATE AND CRYSTALLIZATION OF MALTOSE THEREFROM

This invention relates to a process for obtaining crystalline maltose of extremely high purity, which process can be practiced efficiently and economically on an industrial scale.

Within recent years it has been discovered that the use of a maltogenic enzyme such as beta-amylase in conjunction with the so-called starch debranching enzymes (such as alpha-1,6 glucosidase) which attack the 1,6 linkages of the amylopectin, in the saccharification of starch will produce starch hydrolyzates of much higher maltose content than could be previously obtained with maltogenic enzymes alone. One of the earliest reported inventions in this area is that of U.S. Pat. No. 3,565,765 to Heady et al, which discloses the saccharification of thinned starch substrates, of 30% solids concentration, with maltogenic enzymes plus pullulanase, to obtain hydrolyzates containing up to 80% maltose.

Many others have been active in this field of "high maltose" (i.e. 70% or more maltose) technology, the work going generally in two directions.

(1) toward the preparation of high maltose syrups, for use as such, which will resist spontaneous crystallization (i.e. hazing) at about 80% solids concentration during normal conditions of storage, shipment, etc., and (2) toward the preparation and recovery of maltose per se of the greatest possible purity.

Because the instant invention falls in the second category, only a few of the "syrup patents" need to be considered.

British Pat. No. 1,273,789 to A. E. Staley Manufacturing Company discloses syrups, prepared by saccharifying starch with a maltogenic enzyme and a debranching enzyme, which syrups contain from 60% to 80% maltose and 15% to 35% maltotriose. Those syrups, because of the high maltotriose content in proportion to the maltose content, are resistant to spontaneous crystallization, i.e. hazing, at 80% solids or higher.

British Pat. No. 1,309,834 to Hayashibara Company discloses blending conventional starch hydrolyzates, containing branched oligosaccharides and dextrins, with hydrolyzates which have been treated with debranching enzymes in order to prepare syrups having optimum properties of crystallizability, viscosity, sweetness and hygroscopicity.

British Pat. No. 1,268,081 to A. E. Staley Manufacturing Company discloses the saccharification of thinned starch with a combination of three enzymes, i.e.

(1) a diastase such as beta-amylase or a fungal alpha-amylase, (2) glucoamylase, and (3) alpha-1,6 glucosidase to produce speciality syrups of various saccharide compositions.

Most of the recent work has been done in the area of obtaining maltose per se, and, logically, most of the processes directed toward this end have sought to hydrolyze starch so as to obtain hydrolyzates of the highest amount of maltose possible, with the lowest attendant content of other saccharides, i.e. dextrose, maltotriose, and higher saccharides.

Although the reported processes for preparing these extremely high maltose hydrolyzates are undoubtedly operable and effective, none of them combines those qualities necessary to make up a really good industrial-scale process, i.e. low cost, simplicity of operation and low energy consumption.

Several prior art processes require substrates for saccharification of extremely low solids content, i.e. a maximum of 10% to 15% solids (which processes require, eventually, the removal of large amounts of water), and/or the use of newly developed enzyme sources, which are costly to obtain or prepare. Typical of these processes are those reported in the following references.

U.S. Pat. No. 3,795,584 to Mitsuhashi et al, wherein hydrolyzates of 93% maltose or higher are obtained by saccharifying a liquefied starch substrate having a solids content of less than 15%, with beta-amylase and an alpha-1,6 glucosidase produced from a specific bacterium.

U.S. Pat. No. 3,992,261 to Takasaki et al, discloses microorganisms capable of producing both beta-amylase and alpha-1,6 glucosidase simultaneously from the culture broth, and reports conversion of soluble starch up to 100% maltose equivalent using a substrate with a starch solids content of 10%.

British patent No. 1,268,096 to Hayashibara Company, and U.S. Pat. No. 3,804,715 to Sugimoto et al, (assigned to Hayashibara Company) both relate primarily to processes for the initial liquifaction of the starch slurry, prior to saccharification with maltogenic enzymes and debranching enzymes, and both patents recommend, in lieu of the conventional liquifaction with alpha-amylase, an initial non-enzymatic liquifaction at very high temperatures to produce thinned starch having D.E.'s of less than 5. The U.S. patent also presents a good discussion of many of the problems encountered in the preparation of extremely high maltose hydrolyzates.

In the preparation of high maltose products it is unquestionably desirable to employ, for the saccharification substrate, a liquified starch of as low a D.E. as possible, i.e. preferably below 5 D.E., but the non-enzymatic high temperature processes disclosed in British Pat. No. 1,268,096 and U.S. Pat. No. 3,804,715 require the use of special equipment, resulting in high cost and high energy requirements, and furthermore, if such liquefaction processes are employed using high solids starch slurries the final saccharification products frequently contain large amounts of unconverted starch, resulting in product loss and very low filtration rates, unless additional and costly steps to remove this starch are inserted into the process.

An altogether different approach to the preparation of extremely high purity maltose per se, is reported in U.S. Pat. No. 3,832,285 to Kurimoto, which approach does not make use of debranching enzymes. The patentee first gelatinizes a slurry (15% solids or lower) of starch containing at least 50% by weight amylopectin (and preferably a waxy starch, which consists almost exclusively of amylopectin), and subjects the gelatinized starch to the action of beta-amylase which is free from active alphaamylase, maltase, glucoamylase and isoamylase, whereby only maltose is produced from the non-reducing terminal groups of the starch molecules. The maltose is recovered by dialysing the product against water; although the process produces high purity maltose, the economics make it totally unsuitable for a large-scale industrial operation.

U.S. Pat. No. 3,677,896 to Kurimoto et al discloses and claims preparing starch hydrolyzates having greater than 90% maltose by saccharifying liquefied starch with betaamylase and alpha-1,6 glucosidase, concentrating the hydrolyzate to obtain a massecuite containing maltose crystals, and then spray-drying the massecuite to obtain a dry product. Also disclosed in the patent is the recovery from the massecuite of the microcrystals of maltose which are formed upon concentrating and seeding the massecuite, to obtain crystals of exceptionally high purity; apparently, however, the economics of the process favor the spray-drying of the entire massecuite, rather than recovering the crystals from same.

The patent discloses a number of suitable processes for obtaining the high maltose hydrolyzates, including several which employ relatively high (25% to 35%) solids substrates, but these disclosed processes using high solids generally require very high temperature initial liquifactions, employing special equipment with high energy consumption, or the processes are confined to potato starch (which starch, in contast to most other starches, such as corn starch, is relatively easy to saccharify to high maltose products), or both. Furthermore, alpha-1,6 glucosidases from certain very specific strains of microorganisms are recommended.

Two recently issued U.S. Pat. Nos. 4,028,186 to Sakai and 4,032,403 to Sakai and Tsuyama, disclose interesting techniques for increasing the maltose level of starch hydrolyzates whereby maltose crystals of good size and shape can be recovered in substantially improved yields. U.S. Pat. No. 4,028,186 teaches the use of various fungal alphaamylases either during or after saccharification with maltogenic and debranching enzymes. The operable alphaamylases, which have maltotriose-decomposing activity versus dextrinogenic activity ratios within the range of 0.001 to 0.1 are shown to attack the maltotriose and the higher saccharides of a high-maltose hydrolyzate, resulting in a substantial increase in the maltose content plus a slight increase in the dextrose content. The patentee teaches treating hydrolyzates containing greater than 90% maltose in accordance with the invention followed by crystallization, and discloses that the crystals so obtained (from hydrolyzates having increased maltose contents) are superior in size and form to those obtained from non-treated hydrolyzates.

U.S. Pat. No. 4,032,403 discloses and claims a similar technique but employing a class of enzymes other than the fungal alpha-amylases which enzymes are defined in terms of substrate decomposing activities and other characteristics. These enzymes also attack the maltotriose and higher saccharides, thereby increasing the maltose with a small increase in dextrose.

As in the case in U.S. Pat. No. 4,028,186, the patentees teach treating hydrolyzates of greater than 90% maltose in accordance with their invention followed by crystallization, and describe the crystals thus obtained as being superior to those obtained from hydrolyzates of the prior art.

By far the most economical and practical process for preparing high maltose hydrolyzates, which process can be performed industrially with any type of starch, at starch concentrations of up to 35 or even 40% solids, is the process disclosed in various examples of previously mentioned U.S. Pat. No. 3,565,765 to Heady et al, and which consists of liquefying an aqueous starch suspension, preferably by means of alpha-amylase and preferably to a D.E. of not above 5, followed by saccharification with beta-amylase and pullulanase. Depending upon certain specific conditions, including substrate concentration and enzyme dosage, hydrolyzates are obtained, containing from 75% to about 85%, or even as high as about 87%, maltose, less than about 5% dextrose, the balance being maltotriose and higher saccharides.

Such hydrolyzates are not, of course, sufficiently high in maltose content to be considered themselves "high purity maltose", but they are sufficiently high in maltose to enable pure maltose to be obtained therefrom by a conventional crystallization process, of the type employed to recover other sugars, such as dextrose, from solution, involving adjusting the temperature and solids content of the hydrolyzate to a condition of super-saturation with respect to maltose, inducing crystallization as by the addition of seed crystals, and then gradually decreasing the temperature, with mild agitation, in a conventional crystallizer, to effect the formation of maltose crystals.

However, the crystals so formed from such hydrolyzates are of extremely small size, making their ultimate recovery economically unattractive, and, in some cases, impossible using conventional equipment; this in fact is undoubtedly known by workers in the art, and they have, therefore, striven to increase the maltose content of their hydrolyzates to the highest possible level.

I have discovered that such economically produced hydrolyzates, containing as little as 75% maltose, may be treated under controlled conditions with glucoamylase, whereby the maltotriose and higher saccharides are substantially reduced without any attendant reduction of the maltose content, and that such treated hydrolyzates, when subjected to a conventional crystallization process, yield large amounts of substantially pure maltose crystals having dimensions of at least about 120 microns by 50 microns.

My invention comprises a process for obtaining crystals of maltose of a size at least about 120 microns $\times$ 50 microns, comprising the following steps, (a) treating a starch hydrolyzate, having a maltose content of at least 75% and a viscosity of greater than 400 cps., with glucoamylase under hydrolyzing conditions to reduce the viscosity to below 400 cps., without substantially reducing the maltose content, (b) bringing the thus treated hydrolzate to a state of super-saturation with respect to maltose by increasing the temperature and solids content, and inducing the start of crystallization in the super-saturated solution, (c) gradually lowering the temperature to permit crystallization to continue until at least 25% of the maltose has crystallized, and (d) recovering maltose crystals from the massecuite.

Glucoamylase is, of course, a readily available and inexpensive enzyme, widely used to saccharify starch to dextrose or to dextrose-containing syrups. It is surprising that it, when added to a high maltose syrup, does not immediately cause a reduction in the maltose content. The action of glucoamylase in the process of the invention is particularly unexpected in view of the previously mentioned U.S. Pat. Nos. to Sakai (4,028,186) and Sakai et al (4,032,403), both of which relate to the treatment of maltose syrups with enzymes other than glucoamylase which enzymes are shown by the patentees to be capable of lowering the higher saccharide content without lowering the maltose content of a maltose syrup. U.S. Pat. No. 4,028,186 discloses and claims the use of fungal alpha-amylases which have a maltotriose-decomposing activity versus dextrinogenic activity ratio in the range of 0.001–0.1. Tests of two commercially used glucoamylase preparations, including the one used in the examples of this specification, according to the method set forth in the Sakai patent, showed the ratios to be 0.00043 and 0.00058, well below the lower limit of 0.001. U.S. Pat. No. 4,032,403 discloses a number of enzyme preparations and clearly teaches that, in order to be operable, they must have a maltotriose-decomposing activity versus maltose-decomposing activity ratio of at least 2.5. When the two aforementioned glucoamylase preparations were tested in accordance with the method set forth in this patent the ratios were 0.73 and 0.83, again well below the lower limit disclosed in the patent. It is furthermore very surprising that, following the treatment with glucoamylase, good yields of large maltose crystals can be obtained from hydrolyzates containing less than 90% maltose, and as little as 75% maltose.

The glucoamylase treatment causes a decrease in the maltotriose and the higher saccharides and an increase in the dextrose content with, of course, an attendant decrease in the viscosity of the hydrolyzates. Although a different mechanism may be involved, it appears that the viscosity of the conventional 75%–87% maltose hydrolyzates, although relatively low (generally less than 800 cps. when measured at 57° C. on a 78% solution) may constitute a "limiting factor" with respect to crystal growth. Whatever the mechanism may be, I have discovered that if the viscosity of the hydrolyzate is reduced to below 400 cps. (57° C., 78% solids) a high yield of large maltose crystals can be recovered by "conventional crystallization". Thus the operator can readily determine the optimal extent of the glucoamylase treatment by measuring the viscosity of the hydrolyzate. Throughout the specification the claims, all viscosity values are based on an aqueous solution of 78% solids, at 57° C., unless otherwise stated.

Following is a brief summary of the process of my invention. One first hydrolyzes starch to form a hydrolyzate containing at least 75% maltose and having a viscosity of greater than 400 cps. This hydrolyzate is then further hydrolyzed with glucoamylase until the viscosity has been reduced to below 400 cps. and before any substantial decrease in the maltose content occurs. Finally, the resulting hydrolyzate is brought to a condition of super-saturation with respect to maltose (by adjustment of temperature and solids content), the start of crystallization is induced as by adding seed crystals, after which the crystallization process is continued in conventional manner by slowly reducing the temperature. The large crystals thus obtained are recovered by conventional means, e.g. centrifugation or filtration.

The liquid phase remaining after recovery of the maltose crystals, comprising an aqueous solution of maltose, dextrose, plus minor amounts of higher saccharides, constitutes a valuable "co-product" which can be used as a sweetner in a large variety of food products, e.g., confectionery, ice creams, jams and jellies, etc. In addition to being a valuable product "as is", the solution can be blended with other sweeteners to form a large variety of interesting products for the food industry. If an extremely high-maltose hydrolyzate is employed as the starting material, the liquid phase remaining after the crystallization may contain sufficient maltose to permit a second crystallization, with recovery of additional maltose crystals; however, the principal economic advantages of the invention are realized from using, as a starting material, a maltose hydrolyzate containing from 75% to 85% maltose, and the liquid phase remaining after crystallization from such hydrolyzates will ordinarily not contain sufficient maltose to render a second crystallization practical.

The invention will now be described in more specific detail, including the preferred conditions.

PREPARATION OF THE ORIGINAL HIGH MALTOSE STARCH HYDROLYZATE

The process whereby the starting material hydrolyzate is made is immaterial to the practice of the invention, and any process known in the art is suitable. Naturally, the operator will wish to employ the most economically available process for obtaining the starting material, and the following process is recommended as being particularly suitable for an industrial operation.

An aqueous slurry of any type of starch, having a solids content of from 25% to about 40%, is first liquefied by means of alpha-amylase to a relatively low D.E., not above 10 and preferably not above 5. The liquified product is then subjected to a brief high temperature treatment, i.e., about 100° C. and preferably up to about 140° C., to gelatinize and liquefy completely any remaining starch. This last mentioned high temperature treatment is important because the product is ultimately to be filtered prior to the crystallization process, and any starch remaining after the saccharification step will interfere greatly with the filtration.

Next, the liquefied starch slurry is cooled, the pH is adjusted, and it is saccharified with a maltogenic enzyme and a debranching enzyme. There are, of course, many maltogenic enzymes on the market, such as the various beta-amylases from malt, barley, soya, etc., as well as maltogenic enzymes from *Bacillus Polymixa*. (It is preferred that the maltogenic enzymes employed have a minimum of alpha-amylase activity, in order to avoid, as much as possible, the formation of trisaccharides).

Also, pullulanase debranching enzyme preparations are readily available on the market, two commercial products being those sold by ABM (Untied Kingdom) under the trade name Pullyzyme K 2000, and AMANO (Japan) under the trade name CK 20.

The saccharification reaction is pursued until the desired level of maltose, i.e., at least 75%, is reached; this generally occurs within a period of from about 24 hours to about 48 hours. In the event that traces of starch still remain in the saccharified product, which, if present, will interfere with the subsequent filtration, they can be removed at this stage by means of a brief treatment with a bacterial alpha-amylase.

The starting material which will have a viscosity of greater than 400 cps. is then treated in accordance with the invention, as follows:

SUBSEQUENT GLUCOAMYLASE TREATEMENT TO REDUCE VISCOSITY

The pH is adjusted to 4.0 to 5.5, a glucoamylase enzyme preparation (preferably substantially free from transglucosidase activity) is added, and the product is further saccharified, at a temperature of 45° C. to 70° C. until the viscosity has been reduced to below 400 cps. and before any substantial reduction in the maltose content takes place. (By "substantial reduction" is meant a reduction of 2% or more). The enzymatic action is then terminated, as by boiling.

Alternatively, the glucoamylase can be immobilized and the starting material further hydrolyzed by passing it through a bed of the immobilized enzyme; this technique is illustrated in Example III.

The final hydrolyzate, which will be lower in saccharides of DP3 and higher than the starting material, higher in dextrose, and which will contain substantially the same amount, or even slightly more, of maltose, and will have a viscosity of less than 400 cps., is then subjected to a crystallization process.

As has been mentioned previously, any conventional process for crystallizing a sugar from solution, involving concentration and heating to bring the hydrolyzate to a state of super-saturation with respect to maltose, inducing the start of crystallization (as by adding seed crystals), and then gradually lowering the temperature to permit the crystals to grow, can be employed in order to obtain the crystals. The crystals are then recovered from the liquid phase by conventional means, e.g. centrifugation.

The following examples will illustrate specific methods for practicing the invention. The examples are intended to be illustrative only, and should not be construed as limiting the claims.

Throughout the examples all percentages are by weight, dry basis, unless otherwise noted. Whenever enzyme dosages are expressed in activity units (AU) these are based on 1 kg of dry starch.

The activity of glucoamylase, expressed in activity units, is the number of grams of reducing sugars produced by 1 gram of enzyme in 1 hour at 60° C. and pH 4.3, during an incubation period of a total of 2 hours duration using, as the substrate, a starch hydrolyzate having a D.E. in the range of 10 to 20.

Beta-amylase activity is determined as follows. To 50 mls of a starch hydrolyzate solution of exactly 8% concentration and a 15-20 Dextrose Equivalent is added 5 mls 0.5 molar acetic acid/sodium acetate buffer adjusted to pH 4-6. The mixture is equilibrated at 50° for 15 min., after which the sample of enzyme of known wt. is added. A blank is also prepared, substituting distilled water for enzyme solution. After mixing, the tests are maintained at 50° C. for 55-57 minutes, when 3 drops phenolphtalein indicator are added. After precisely 60 minutes the flask is removed from the heating bath and immediately neutralized to first faint pink color by addition of 1% sodium hydroxide solution, followed by addition of a further 0.5 ml. The solution is then cooled to room temperature and diluted to exactly 100 mls.

The reducing of sugars of the sample are then determined by the Schoorl method, a stardard method used throughout the industry.

The activity is calculated from the following formula:

Enzyme activity, units/gm. =
$$\frac{\text{Sample } R.S. (g) - \text{Blank } R.S. (g) \times 10}{\text{Sample wt. (g)}}$$

Where R.S.=total reducing sugars in the sample of enzyme taken for analysis

Pullulanase activity is determined as follows. 1 g. of pullulan is boiled in 70 ml. distilled water for 5 minutes, cooled, 10 ml. molar acetate buffer pH 5.0 is added and the whole diluted to 100 ml. It is finally filtered.

1 ml. of the pullulan solution is maintained at 50° C. for 5 minutes, after which 1 ml. of enzyme solution is added and reaction allowed to proceed for exactly 10 minutes. The reaction is stopped by adding 2 ml. of DNS reagent, prepared by dissolving 1 g. 3.5 dinitro salicylic acid in 16 ml. 10% sodium hydroxide solution to which 30 g. Rochelle salt is added, and finally diluting to 100 ml.

A blank is prepared by adding 2 ml. DNS reagent to the substrate before the enzyme.

The two samples are placed in a boiling water bath for exactly 5 minutes, then cooled rapidly and 10 ml. distilled water added with mixing.

The optical density of the test solution is read against the blank using 2 cm. cells at a wavelength of 540 mu. An optical density if 0.325 is given by 0.4 pullulanase activity units. Therefore several dilutions are made and tested and a graph of optical density against enzyme concentration is plotted. That concentration which gives an optical density of 0.325 contains by definition 0.4 pullulanase activity units. Therefore activity of the sample is calculated from the following formula:

$$\text{Activity (Pullulanase Units)} = \frac{1000}{\text{mg, enzyme in test}} \times \frac{0.4}{10}$$

The term "DP" means "degree of Polymerization".

EXAMPLE I

Starting material containing 75% maltose.

1. Preparation of Starting Material (a) Liquefaction

To 500 liters of a 35% d.s. (dry substance) aqueous slurry of regular corn starch was added $CaCl_2$ and NaCl to provide 150 ppm $Ca^{++}$ plus 300 ppm $Cl^-$. The pH of the slurry was 5.8-6.0. 2000 AU per Kg. of starch of a bacterial alpha-amylase (Termamyl, by NOVO) was added, and the slurry was transferred to a jacketed autoclave (heated by indirect steam) where it was subjected to a temperature of 88°-92° C. for about 30 minutes. The slurry was then subjected to a "heat shock" treatment to liquefy any remaining starch and to destroy the enzyme by closing the autoclave whereby the temperature was brought to 140° C. over a period of about 20 minutes. The slurry was held at that temperature for about 10 minutes. The liquefied product had a D.E. of 5.

(b) Saccharification

The liquefied starch was cooled to about 55° C. and transferred to a saccharification tank where the pH was regulated to 5.5-5.8. Then 100 AU of beta-amylase (Biozyme M2 from AMANO) and 1600 AU of pullulanase were added, and the product was incubated for 40 hours at the end of which time the hydrolyzate contained 75% maltose. The hydrolyzate was filtered and then refined with carbon. The characteristics of the product are set forth in Table I, under the heading "Starting Material".

The refined hydrolyzate was divided into two equal portions, one portion being reserved for a comparative crystallization, the other being treated in accordance with the invention as follows.

2. Glucoamylase Treatment

The pH was adjusted to 4.2 and 160 AU of a glucoamylase enzyme preparation from *Aspergillus niger* was added, and the product was incubated at 55°–60° C. for four hours, after which the enzyme was inactivated by boiling the hydrolyzate and then removed by carbon filtration. The characteristics of the resulting product are set forth in Table I, under the heading "After Glucoamylase Treatment".

The product, as well as the refined starting material, were then subjected to identical crystallization processes as follows.

3. Crystallization

A pilot plant crystallizer was used for the parallel crystallization trials, composed of two horizontal vessels of 20 liters practical capacity each equipped with a double jacket and a scraper type agitator. Agitation speed is of 3 rpm and by means of an external boiler and temperature programmer hot water can be circulated in the jackets so as to drop the temperature down from the original at a fixed and equal rate for the two vessels.

The initial crystallization trials necessarily employed outside obtained maltose crystals as seed; in order to obtain meaningful comparative data a series of hydrolyzates were prepared and subjected to successive crystallization trials, by emptying 75% of the crystallizer when the "low" temperature point was reached while keeping the remaining 25% of mass as seed for the next trial. The comparative crystallization data were recorded after crystal equilibrium had been reached.

For the crystallization the hydrolyzates were evaporated to 78% d.s and placed in the crystallizer. The temperature was brought initially to 57° C. after which it was decreased at a constant rate of 0.16° C. per hour until it reached the final temperature of 45° C. The massecuite was removed and the crystals recovered by centrifugation.

The comparative crystallization data are given in Table I.

TABLE I
(75% maltose hydrolyzate)

| | Starting material (Control) | After Glucoamylase Treatment (Invention) |
|---|---|---|
| Hydrolyzate characteristics | | |
| D.E. | 52 | 64 |
| Dextrose | 2% | 17% |
| Maltose | 75% | 75% |
| DP 3 | 17% | 5% |
| DP >3 | 6% | 3% |
| Viscosity (78 d.s. 57° C.) | 715 cps. | 370 cps. |
| Ash (% dry basis) | .45% | .45% |
| Color (solution color × 100) | 1.4 | 1.4 |
| Crystallization data | | |
| Purity of unwashed cake (1) | X | 83% |
| Yield as such | X | 26% |
| Yield as 100% maltose cryst. | X | 22% |
| Crystal size | 20 × 5 microns | 120 × 50 |

X: Could never be recovered due to too fine crystals
(1): "Purity of unwashed cake" refers to the maltose content in the crystal cake separated from the crystallizer massecuite.

The liquid phase remaining after recovery of the dextrose crystals constituted a very pleasant tasting syrup having the following saccharide composition.

| DP 1 | 21.8% |
|---|---|
| DP 2 | 68% |
| DP 3 | 6.4% |
| DP 4 and higher | 3.8% |

This syrup could be used as a sweetner in a large number of food products, E.G., confectionery, ice cream, jam and jellies, dairy products or the like. In addition to being useful as a syrup per se, it could also, of course, be blended with various other sweetners to form an extremely large variety of valuable products.

EXAMPLE II

Starting material containing 80% maltose.

Example I was repeated, except the saccharification reaction was conducted using 200 AU of beta-amylase, and 1600 AU of pullulanase, to form a hydrolyzate containing 80% maltose. The beta-amylase employed was a blend of a high purity beta-amylase (Biozyme M2) and a vegetable beta-amylase (high diastatic malt extract of 1500° Lintner).

The hydrolyzate was refined with ion exchange resins instead of carbon.

The glucoamylase treatment was as in Example I except the time was only two hours. The crystallization step was as in Example I.

The data from this example are tabulated in Table II.

TABLE II
(80% maltose hydrolyzate)

| | Starting material (Control) | After Glucoamylase Treatment (Invention) |
|---|---|---|
| Hydrolyzate characteristics | | |
| D.E. | 54 | 61 |
| Dextrose | 3% | 12% |
| Maltose | 80% | 80% |
| DP 3 | 15% | 6% |
| DP >3 | 2% | 2% |
| Viscosity | 415 cps. | 239 cps. |
| Ash | .01% | .01% |
| Color | .7 | .7 |
| Crystallization data | | |
| Purity of unwashed cake | 87% | 93% |
| Yield as such | 41% | 43% |
| Yield as 100% maltose crystals | 35% | 40% |
| Crystal size | 80 × 20 microns | 150 × 60 microns |

The liquid phase remaining after recovery of the crystals had the following saccharide composition:

| DP 1 | 20% |
|---|---|
| DP 2 | 66.6% |
| DP 3 | 10% |
| DP 4 and higher | 3.4% |

As was the case with the liquid phase remaining in Example I, this product was also a very pleasant tasting syrup, having a great many uses.

EXAMPLE III

Use of immobilized glycoamylase for viscosity reduction.

In using glucoamylase to reduce the viscosity of the hydrolyzate care must be taken to stop completely the enzymatic reaction at the right time, i.e., when the desired viscosity reduction has been achieved but without any reduction in maltose content. This can be a problem in an industrial scale operation using large volume incubators and inactivating the enzyme by boiling; because of the length of time required to bring the temperature of the entire contents of the incubator to the "inactivation temperature". This problem can readily be avoided by conducting the reaction continuously through a bed or column of glucoamylase immobilized onto a suitable carrier material, and this example illustrates such a technique.

1. Preparation of Starting Material (a) Liquefaction

In this example a continuous liquefaction process was employed. 800 liters of a 35% solids corn starch slurry, plus alpha-amylase, was prepared as in Example I, and it was continuously liquefied by sending it through a series of heaters and holding columns as follows:

1. Pre-heat the slurry at 95° C. in about 30 seconds by means of a tubular heat exchanger.
2. Holding in a jacketed column at 90°-95° C. for 45 minutes.
3. Heat in a second heat exchanger up to 140° C.
4. Holding at 140° C. in an insulated baffled column for 12 minutes.
5. Flash to atmosphere in a cyclone, cool to 55°-60° C. by pumping through a plate heat exchanger with 50° C. water circulation, then pump to a batch saccharification tank. The saccharifying enzymes (pullulanase and beta-amylase) are injected into the stream going into the tank.

The liquefied starch had a D.E. of 8, and contained about 40% apparent starch when tested by iodine coloration.

(b) Saccharification

The enzyme dosage was 1600 AU of pullulanase and 100 AU of malt extract. No pH adjustmemt was made prior to enzyme addition (the original slurry pH being 5.8–6.0). During the saccharification the pH dropped to 5.5, and it was maintained at that level with a pH controller.

The saccharification was conducted at 55°-60° C. for 24 hours, after which the product had the following composition.

| | |
|---|---|
| D.E. | 53 |
| Dextrose | 1.5% |
| Maltose | 77 |
| DP 3 | 14% |
| DP >3 | 7.5% |
| Apparent starch | 1.5% |

Because the apparent starch content would have rendered filtration difficult, it was removed by adding 250 untis of bacterial alpha-amylase (Termanyl) and sending the product through the heat exchanger and holding coil, which treatment hydrolyzed all of the starch without any significant change of the sugar composition.

The hydrolyzate was filtered and then refined with both carbon and ion exchange to reduce the impurities to a minimum and thereby avoid any risk of inactivating the immobilized enzyme system.

2. Glucoamylase Treatment

The glucoamylase was immobilized by ciruclating it over a 500 ml column of XN 1009, an adsorbant manufactured by Rohm and Haas (Macroreticular polystyrenic anion exchanger, the anion exchange activity of which was neutralized by buffering it at pH 4.2).

Excess of unbound enzyme was washed out of column prior to start up.

A series of experimental runs were made, wherein the refined hydrolyzate was sent over the immobilized enzyme column at various flow rates to determine the right conversion conditions.

The results of these trials are tabulated in Table III.

TABLE III

| Flow rate on Column (Bed Volumes/Hour) | D.E. | Dextrose | Maltose | DP 3 | Higher Saccharides | Viscosity |
|---|---|---|---|---|---|---|
| Original Hydrolyzate | 53 | 1.7 | 77 | 14 | 7.3 | 650 cps |
| (feed to column) | | | | | | |
| .70 BV/H | 92.3 | 80.5 | 17.5 | 1.6 | .4 | 55 |
| 1.70 BV/H | 69.5 | 31 | 66.2 | 1.8 | 1.0 | 90 |
| 2.2 BV/H | 65.4 | 19.5 | 75.2 | 3.5 | 1.8 | 100 |
| 2.6 BV/H | 62.6 | 16 | 78.3 | 4.0 | 1.7 | 120 |
| 2.7 BV/H | 62.3 | 16 | 78.1 | 5.5 | .4 | 110 |
| 2.8 BV/H | 61.6 | 15.5 | 78.5 | 4.5 | 1.5 | 110 |

As can be seen from Table III, in this case the optimum flow rate was from 2.6 to 2.8 bed volumes per hour, and this technique even produced a slight increase in the maltose content of the hydrolyzate. A flow rate of 2.2 bed volumes per hour was also operable, as it resulted in only a slight reduction of the maltose content.

The hydrolyzates containing 75.2% and more maltose could easily by crystallized to produce good yields of large maltose crystals, as in the previous examples.

Of course, many suitable materials and techniques for immobilizing enzymes are known in the art, and could be successfully applied in the practice of the invention. The foregoing data are presented merely as a guide to the skilled operator, who will be able readily to select the optimum conditions for his particular operation.

I claim:

1. A process for obtaining crystals of maltose of a size of at least 120 microns ×50 microns, comprising the following steps:
   A. treating a starch hydrolyzate, having a maltose content of at least 75% and a viscosity of greater than 400 cps., with glucoamylase under hydrolyzing conditions to reduce the viscosity to below 400 cps., without substantially reducing the maltose content,
   B. bringing the thus treated hydrolyzate to a state of super-saturation with respect to maltose by increasing the temperature and solids content, and inducing the start of crystallization in the super-saturated solution,
   C. gradually lowering the temperature to permit crystallization to continue until at least 25% of the maltose has crystallised, and
   D. recovering maltose crystals from the massecuite.

2. The process of claim 1, wherein the initial starch hydrolyzate has been prepared by first liquefying an aqueous slurry of starch, having a solids content of 25% to 40%, with alpha-amylase to a D.E. of not above 10%, and then saccharifying the liquefied starch with beta-amylase plus a starch debranching enzyme.

3. The process of claim 2, wherein said starch debranching enzyme is pullulanase.

4. The process of claim 1, wherein the glucoamylase treatment is conducted at a pH of from 4.0 to 5.5, a temperature of from 45° C. to 70° C., an enzyme dosage of from 100 to 250 AU per Kg. dry substance, and for a time period sufficient to reduce the viscosity to below 400 cps. without any substantial reduction of the maltose content.

5. The process of claim 1, wherein the glucoamylase is in immobilized form and the hydrolyzate is treated by passing it through a mass of the immobilized glucoamylase at a pH of 4.0 to 5.5 and a temperature of 45° C. to 70° C.

6. The process of claim 1, wherein the starch hydrolyzate has a maltose content of about 80%.

* * * * *

UNITED STATES PATENT AND TRADEMARK OFFICE
CERTIFICATE OF CORRECTION

PATENT NO. : 4,199,372
DATED : April 22, 1980
INVENTOR(S) : Raoul G. P. Walon

It is certified that error appears in the above-identified patent and that said Letters Patent are hereby corrected as shown below:

Column 1, line 60, "speciality" should read --specialty--.
Column 3, line 24 "contast" should read --contrast--.
Column 6, line 45, "Untied" should read --United-- and in line 61 "TREATEMENT" should read --TREATMENT--.
Column 7, line 51, first occurrence should be deleted and in line 52 "stardard" should read --standard--.
Column 8, line 14 "if" should read --of--.
Column 9, line 51 "Crystalllization" should read --Crystallization-- and in line 61 "dextrose" should read --maltose--.
Column 11, line 53 "untis" should read --units-- and "(Termanyl)" should read --(Termamyl)-- and in line 64 "ciruclating" should read --circulating--.

Signed and Sealed this

Eighteenth Day of November 1980

[SEAL]

Attest:

Attesting Officer

SIDNEY A. DIAMOND

Commissioner of Patents and Trademarks